US012721503B2

(12) United States Patent
Schütz

(10) Patent No.: US 12,721,503 B2
(45) Date of Patent: Sep. 1, 2026

(54) ENDOSCOPE WITH ONE STEERING INPUT ELEMENT FOR TWO BENDING PLANES

(71) Applicant: AMBU A/S, Ballerup (DK)

(72) Inventor: Jakob Schütz, Neusäß (DE)

(73) Assignee: AMBU A/S, Ballerup (DK)

( * ) Notice: Subject to any disclaimer, the term of this patent is extended or adjusted under 35 U.S.C. 154(b) by 684 days.

(21) Appl. No.: 18/073,129

(22) Filed: Dec. 1, 2022

(65) Prior Publication Data

US 2023/0172440 A1 Jun. 8, 2023

(30) Foreign Application Priority Data

Dec. 2, 2021 (DE) ..................... 10 2021 131 850.5

(51) Int. Cl.

*A61B 1/005* (2006.01)
*A61B 1/00* (2006.01)
*A61B 1/05* (2006.01)

(52) U.S. Cl.

CPC ........ *A61B 1/0052* (2013.01); *A61B 1/00042* (2022.02); *A61B 1/00045* (2013.01); *A61B 1/00128* (2013.01); *A61B 1/0057* (2013.01); *A61B 1/05* (2013.01)

(58) Field of Classification Search

CPC ............ A61B 1/00042; A61B 1/00052; A61B 1/0052

See application file for complete search history.

(56) References Cited

U.S. PATENT DOCUMENTS 4,461,282 A 7/1984 Ouchi et al.
4,924,852 A * 5/1990 Suzuki ................. A61B 1/0052 600/150
4,932,394 A 6/1990 Nanaumi
4,947,827 A 8/1990 Opie et al.
5,738,631 A 4/1998 Konstorum (Continued)

FOREIGN PATENT DOCUMENTS

DE 10222686 A1 11/2002
DE 19758596 B4 7/2005

(Continued)

OTHER PUBLICATIONS

German Search Report received for DE Application No. 102021131850.5, mailed on Aug. 23, 2022, 10 pages (5 pages of English Translation and 5 pages of Original Document).

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

An endoscope (1) including a handle (2), an insertion cord (3), and a steering mechanism, the insertion cord (3) including an insertion tube (4), a bending section (5) and a distal tip unit (6), the steering mechanism including a manually operable steering input element (7) to receive a rotational input by a user and being connected to a control shaft, which is rotatably supported at the endoscope handle (2) and a steering switch mechanism (13) configured to switch a coupling state of the steering input element (7) at least between a first mode of operation, in which the steering mechanism bends the bending section (5) in a first bending plane, and a second mode of operation, in which the steering mechanism bends the bending section (5) in a second bending plane.

20 Claims, 6 Drawing Sheets

(56) References Cited

U.S. PATENT DOCUMENTS 8,591,405 B2 11/2013 Hoshino
8,808,168 B2 8/2014 Ettwein et al.
9,820,634 B2 11/2017 Simchony et al.
10,165,931 B2 1/2019 Petersen et al.
2001/0034472 A1 10/2001 Fujii et al.
2003/0023143 A1 1/2003 Abe et al.
2006/0252993 A1 11/2006 Freed et al.
2009/0227841 A1* 9/2009 Miyako .................. A61B 1/009 600/139
2011/0295242 A1 12/2011 Spivey et al.
2012/0116166 A1 5/2012 Matsuura et al.
2013/0205937 A1* 8/2013 Arai .................. G02B 23/2476 74/527
2014/0012087 A1* 1/2014 Omoto .................. A61B 1/018 600/146
2014/0046129 A1 2/2014 Boutillette et al.
2014/0066706 A1 3/2014 Mcweeney et al.
2015/0119801 A1 4/2015 Grewe et al.
2015/0164305 A1 6/2015 Kohno
2015/0313447 A1* 11/2015 Arai .................. G02B 23/2476 600/146
2016/0073856 A1* 3/2016 Saito .................... A61B 1/0057 600/149
2016/0100742 A1* 4/2016 Okamoto ............. A61B 1/0016 600/152
2016/0316997 A1 11/2016 Viebach et al.
2018/0049623 A1 2/2018 Golden et al.
2019/0239728 A1 8/2019 Do et al.
2020/0405126 A1 12/2020 Golden et al.
2021/0161371 A1* 6/2021 Akui ...................... A61B 18/24
2021/0212553 A1* 7/2021 Appling ............. A61B 1/00128
2021/0251468 A1 8/2021 Takeshi
2021/0338051 A1 11/2021 Nielsen et al.
2021/0369082 A1 12/2021 Durant et al.
2021/0393115 A1* 12/2021 Sciortino ........... A61B 1/00042
2022/0369901 A1* 11/2022 Powell ................. A61B 1/0057

FOREIGN PATENT DOCUMENTS

DE 102013226591 A1 6/2015
DE 102016121056 A1 5/2018
EP 2508120 A1 10/2012
EP 2537452 A1 12/2012
EP 1737335 B1 5/2013
EP 2288284 B1 5/2016
EP 2417898 B1 12/2016
EP 2883491 B1 4/2017
EP 1956962 B1 9/2020
EP 3903661 A1 11/2021
EP 3903662 A1 11/2021
JP 61-106125 A 5/1986
JP 2002-345742 A 12/2002
WO 2018/159555 A1 9/2018
WO 2020/031293 A1 2/2020
WO 2020/146812 A1 7/2020
WO 2021/219832 A1 11/2021
WO 2022/268891 A1 12/2022

* cited by examiner 15
8
22a
19a
14
10
23a
18a
21a
17a
Fb
24a
11a
9

2
8
22a
19a
17a
15
14
23a
10
18a
21a
7
9
11a
Fb
Fo
24a 2
8
22a
19a
15
14
23a
10
21a
17a
18a
7
Fo
9
11a
24a 8
13
26
25
2
14
9
7

ENDOSCOPE WITH ONE STEERING INPUT ELEMENT FOR TWO BENDING PLANES

CROSS-REFERENCE TO RELATED APPLICATIONS

This application claims priority from and the benefit of German Patent Application No. DE 10 2021 131 850, filed Dec. 2, 2021, said application incorporated by reference herein in its entirety.

TECHNICAL FIELD

The present disclosure relates to an endoscope comprising a handle and a steering mechanism including a manually operable steering control provided to swivel a distal tip in two planes.

BACKGROUND

Steerable endoscopes often have a proximal endoscope handle and a distal insertion cord including a bending section and a distal tip unit. In order to deflect the distal tip unit, the bending section can be bent or manipulated by pulling one or more pulling/steering wires, which extend into the insertion cord of the endoscope and which have distal portions attached to the bending section.

Typically, in an endoscope, which allows four-way-bending, four pulling wires may be provided, which are circumferentially offset with respect to each other by 90°, and pulling either one of the pulling wires/steering wires will result in a bending motion in a corresponding direction. Thus, two degrees of freedom (two bending planes) are provided with one degree of freedom comprising an up/down movement of the bending section effected by pulling one of two diametrically opposing pulling wires, and another degree of freedom comprising a left/right movement of the bending section effected by pulling one of two other diametrically opposing pulling wires.

Such endoscopes are generally provided with two steering input wheels (manually operable wheels/wheel manipulators) at the endoscope handle, with one of the steering input wheels being provided to control an up/down bending and the other one of the steering input wheels being provided to control a left/right bending. The steering input wheels or wheel manipulators are coaxially arranged (stacked next to each other) adjacent to a handle housing. Each steering input wheel is connected to a control wheel, such as a sprocket or wire drum, which is connected to two of the steering wires, e.g. via a chain engaging the sprocket or by winding the wire around the drum. Thus, the steering input wheel is rotated to rotate the control wheel, which results in a pulling of the one (first) wire connected thereto and a loosening of the other (second) wire connected thereto.

There are surgical techniques that allow the endoscope handle to be held while manipulating the steering input wheels with only one hand. However, these are not applicable to surgeons with small hands because they cannot fully reach both steering input wheels.

Further, such endoscopes may have braking mechanisms including brake input elements or brake activators. In particular, one brake mechanism exists for braking each wheel manipulator. When the brake mechanisms are applied, the position of the wheel will be fixed in the current orientation. This allows holding the distal tip in a desired orientation without holding the steering input wheels manually. The brake input element or brake activator for braking the up-down control wheel is typically a lever and for braking the left-right control wheel is a rotatable knob. To enable and disable the brake system a second hand is needed.

Prior art can e.g. be found in U.S. Pat. No. 5,738,631 A which discloses an endoscope comprising a handle and an insertion cord including a 4-way bendable section. The bendable section is controlled via wires connected to spur gears driven via control knobs fixed to concentric shafts respectively for up-down or left-right steering. Further, the endoscope includes a ratchet unit operated via a lever-controlled shaft and including a cam surface, which is rotatable for selectively pressing spring-loaded pins towards the corresponding spur gears to engage and block them. In this manner, both, neither or only the first spur gear is blocked Further, U.S. Pat. No. 4,461,282 A discloses an endoscope having a handle and an insertion cord with a bending or curving section, which can be bent in two planes via a steering mechanism including two separate driving trains. Each driving train includes a wire connected to and driven by an angle adjusting knob via a locking device. Further, a switching mechanism including a locking device for locking both driving trains simultaneously and two clutch mechanisms are provided for switching between driving modes of any of the two driving trains. The clutch mechanisms are actuated via lever-like second wheels for selectively unlocking one of the driving trains.

From U.S. Pat. No. 4,932,394 A an endoscope having a handle and an insertion cord with a bending section is known, which can be bent in two planes via a steering mechanism including two separate driving trains. Each driving train includes a wire connected to and driven by an angle adjusting knob via a locking device. By pulling one or both of the angle adjusting knobs, the respective locking devices and thus, steering, is locked.

US 2001/0034472 A1 discloses an endoscope with two separate driving trains including separate angle knobs, shafts and wire drums for bending a bendable section of an insertion cord. Further, two separate locking mechanisms are provided including a knob or lever operable to translate a pressure element against a friction pad to lock the corresponding driving train.

Further prior art is known from EP 2 220 991 B1 which relates to an endoscope having a handle and an insertion cord including a bending section. The latter is bendable via two separate driving trains including steering wires wound on drums driven via control knobs. Further, a catch mechanism is provided, latching the control wheel in a locked position and opened by a driving pin extending through the control knob, such that by turning said knob, the latching is opened.

EP 2 288 284 B1 and US 2020/0405126 A1 disclose an endoscope having a handle and an insertion cord including a bending portion, which is controllable via steering wires connected to manually controllable knobs via pulleys. The knobs and pulleys are connected to drive members lockable via frictional brake members, which can be displaced radially to provide a friction contact and which are actuated via lock levers.

Further, U.S. Pat. No. 8,591,405 B2 discloses an endoscope having an insertion portion with a portion bendable via steering wires controlled via a manually operable knob. The knob can be locked or braked via a frictional engagement actuated via a brake lever or a brake knob. The brake lever drives a rotatable element having a cam groove defined by a circumferential arm for guiding two rotationally fixed plates towards each other in order to clamp a friction plate which is connected to the manually operable knob.

BRIEF DESCRIPTION OF THE DISCLOSURE

In view of the above-described problems it is an object of the present disclosure to provide an endoscope which shall reduce or avoid the disadvantages of the prior art. In particular, it is an object of the disclosure to provide an endoscope with a steering mechanism for steering a bending section of an insertion cord in at least two different bending planes, with said steering mechanism being particularly easy to use/handle even for users with small hands.

In detail, the present disclosure relates to an endoscope comprising: a proximal endoscope handle; an insertion cord extending from the endoscope handle and configured to be inserted into a patient's body cavity, the insertion cord comprising an insertion tube, a bending section and a distal tip unit; and a steering mechanism configured to swivel the distal tip unit by bending the bending section in a first bending plane and in a second bending plane, the steering mechanism comprising: a manually operable steering input element being provided for receiving a rotational input by a user; and a steering switch mechanism configured to switch a coupling state of the steering input element at least between a first mode of operation, in which the steering mechanism is configured for bending the bending section in the first bending plane via the steering input element, and a second mode of operation, in which the steering mechanism is configured for bending the bending section in the second bending plane via the steering input element. Of course since the steering input element, or steering wheel, is part of the steering mechanism, the coupling state of the steering input element is also a coupling state of the steering mechanism, which is structured to bend the bending section on the first or second planes depending on the coupling state.

Expressed in other words, the present disclosure relates to an endoscope, which is preferably a single-use endoscope, with an insertion cord having a bending section which is bendable in a first bending plane and in a second bending plane different from the first bending plane, in order to swivel a distal tip unit of the insertion cord in said first and second bending planes. The endoscope has a steering mechanism including a manually operable steering input element which can selectively be operated at least in a first mode of operation for bending the bending section in the first bending plane and a second mode of operation for bending the bending section in the second bending plane. That is, the steering mechanism is a gearing (also called a single wheel gearing) that allows to manipulate bending in both bending planes with exactly one steering input element. Preferably, there is also provided a neutral state of the steering switch mechanism, in which neither bending the bending section in the first bending plane nor bending the bending section in the second bending plane is possible.

The idea underlying the present disclosure relates to the following observation. In order to maneuver related art four-way-bending endoscopes in e.g. endoscopic retrograde cholangiopancreatography (ERCP), a primary function of the distal tip deflection via the steering input elements/steering input wheels is to get a camera and an elevator mechanism at the distal tip unit of the endoscope into a correct position and orientation. For that, it is usual to use only one of the steering input elements to control bending in only two (diametrically opposing) directions until the end position is nearly reached. The second steering input element for controlling the other two bending directions are then used for fine adjustment. Thus, it is often not necessary to manipulate both steering input elements or to bend the bending section in two different directions at the same time in related art endoscopes.

Advantageously, an endoscope according to the present disclosure has a particularly simple user interface for controlling the bending section. In particular, a number of parts which the user can manipulate is reduced. Accordingly, the endoscope according to the present disclosure is both simple to use and is cost efficient in manufacture and assembly. Additionally, the user is provided with better access to the steering input element compared to conventional related art endoscopes, since only one steering input element needs to be operated in order to control the bending of the bending section in both bending planes, i.e. the user's fingers do not have to reach a second steering input element. Thus, the steering input element may be arranged directly adjacent to a housing of the endoscope handle/to a grip portion of the endoscope handle and may be easily reachable. Also, the steering input element may be relatively large to be easily graspable.

Preferably, the steering input element is thus the only manually operable element adapted/configured to drive/actuate a bending of the bending section. In other words, preferably exactly one single steering input element is provided which is adapted to drive the bending of the bending section in the at least two bending planes. The first bending plane and the second bending plane are preferably orthogonal to each other.

The manually operable steering input element is preferably connected to a control shaft, which is especially preferred rotatably supported at the endoscope handle/a housing of the endoscope handle. The terms "axially", "circumferentially" and "radially" as used in the present disclosure relate to an axis of the control shaft if not explicitly stated otherwise. The manually operable steering input element may be accessible for a user at an outer side of a housing of the endoscope handle. The steering input element may e.g. be formed as a wheel or knob or a lever. In particular, the steering input element is non-rotatably/fixedly connected to the control shaft. The control shaft is preferably non-translatable relative to the endoscope handle/to the housing of the endoscope handle.

Preferably, the steering mechanism comprises a first control wheel connected to a first steering wire, which extends through the insertion cord and is provided for controlling a bending movement of the bending section in the first bending plane. Moreover, the steering mechanism may have a second control wheel connected to a second steering wire, which extends through the insertion cord and is provided for controlling a bending movement of the bending section in the second bending plane.

The steering switch mechanism preferably comprises a first coupling portion formed between the steering input element and the first control wheel and adapted for coupling the steering input element to the first control wheel. Further, the steering switch mechanism preferably comprises a second coupling portion formed between the steering input element and the second control wheel and adapted for coupling the steering input element to the second control wheel.

Preferably, the first and second control wheels are mounted on the (same) control shaft (i.e. one single control shaft) to be selectively driven via said control shaft. In particular, the steering switch mechanism may selectively open or close the first coupling portion and the second coupling portion (i.e. the coupling portions). In particular, the coupling portions (or braking portions which are described in detail below) are closed when a force is transmitted via the coupling portions (or braking portions). E.g. the first coupling portion is closed, when a rotation of the first control shaft is transmitted via the first coupling portion to the first control wheel. On the other hand, the coupling portions (or braking portions) are considered open when no force is transmitted via the coupling portions (or braking portions). Preferably, the coupling portions open and close in an axial direction. Thus, relatively little radial space is needed for the coupling portions, which allows further adaptation of the endoscope handle for users with small hands. The first coupling portion may include a first friction fit arrangement (being a friction connection pairing) such as a stack of friction discs. The second coupling portion may include a second friction fit arrangement such as another stack of friction discs. Alternatively, the first coupling portion and the second coupling portion may respectively provide an engagement connection pairing instead of a friction pairing.

The first control wheel and the second control wheel (i.e. the control wheels) are preferably formed as wire drums, on which the steering wires may be wound. Alternatively, the control wheels may e.g. be sprockets connected to the steering wires via gear racks. The first control wheel and the second control wheel are preferably arranged symmetrically with respect to each other. This is a particularly simple design.

Preferably, the steering switch mechanism further has a first braking portion adapted to (non-rotatably) connect the endoscope handle/a housing of the endoscope handle (directly or indirectly) to the first control wheel for braking said first control wheel. Further, the steering switch mechanism may have a second braking portion adapted to (non-rotatably) connect the endoscope handle/a housing of the endoscope handle (directly or indirectly) to the second control wheel for braking said second control wheel. Accordingly, the first braking portion and/or the second braking portion (i.e. the braking portions) may be closed to prevent a rotation of the first and/or second control wheels or opened to allow a rotation thereof. This is particularly advantageous, since an unintentional bending of the bending section e.g. due to gravity or residual friction within the otherwise open first and/or second coupling portions can be avoided.

The first braking portion may include a third friction fit arrangement (i.e. a friction connection pairing) such as a stack of friction discs. Said third friction fit arrangement may connect the endoscope handle/the housing of the endoscope handle directly or indirectly to the first control wheel. The second braking portion may include a fourth friction fit arrangement such as another stack of friction discs. Said fourth friction fit arrangement may connect the endoscope handle/the housing of the endoscope handle directly or indirectly to the second control wheel. Alternatively, the first braking portion and the second braking portion may respectively provide an engagement pairing instead of a friction pairing as described above. Preferably, the braking portions open and close in an axial direction. Thus, a simple braking mechanism which requires relatively little radial space may be provided.

It is advantageous, if the steering switch mechanism further comprises a first biasing element biasing the first control wheel (relative) to the housing of the endoscope handle such that the first braking portion is biased to be closed, e.g. in a neutral state/position of the steering switch mechanism. Moreover, the steering switch mechanism may comprise a second biasing element biasing the second control wheel (relative) to the housing of the endoscope handle such that the second braking portion is biased to be closed, e.g. in a neutral state/position of the steering switch mechanism. Such a biasing element makes it thus possible to provide a mechanism for automatically closing the first and/or the second braking portions. Thus, it is easy to maintain a bending state of the bending section without a user growing tired. A duration in which the user needs a second hand for manipulating the distal tip and for simultaneously enabling and disabling the brakes of an endoscope is minimized. Preferably, the biasing element is a compression spring. Further preferably, the first and second biasing elements are essentially the same (i.e. have the same dimensions and elastic properties).

In particular, the steering switch mechanism may thus be adapted to switch a coupling state of the steering input element to a neutral state, in which the first braking portion, and preferably the second braking portion, is/are closed in order to brake the first control wheel, and preferably the second control wheel, and in which the first coupling portion and the second coupling portion are open and uncoupled from the steering input element. Accordingly, a risk of unintentional bending of the bending section in the first and/or in the second bending plane is further minimized.

Preferably, when the steering switch mechanism is in the neutral state, a side of the first control wheel and a side of the second control wheel are arranged essentially symmetrically with respect each other. In particular, the first and second control wheels are essentially identical. This ensures a balanced operation of the steering mechanism. Moreover, an assembly may be less complex and manufacturing costs may be reduced.

Advantageously, the first control wheel may form a first wheel side braking surface adapted to connect to a first handle side braking surface as part of the first braking portion. Further, the first control wheel may form a first wheel side coupling surface adapted to connect with a first shaft side coupling surface as part of the first coupling portion. The first wheel side braking surface and the first wheel side coupling surface are preferably oriented in a first axial direction, further preferably towards a supporting flange that is non-rotatably connected to the control shaft and is described in more detail below. Similarly, the second control wheel may form a second wheel side braking surface adapted to connect with a second handle side braking surface as part of the second braking portion. Further, the second control wheel may form a second wheel side coupling surface adapted to connect to a second shaft side coupling surface as part of the second coupling portion. The second wheel side braking surface and the second wheel side coupling surface may be oriented in a second axial direction, particular opposite to the first axial direction. In this case, the first coupling portion and the first braking portion may (simultaneously) be biased towards a closed position via a single biasing element. Additionally, this axially assembled structure of the steering mechanism is easy and thus cost-efficient to assemble.

The first handle side braking surface and the second handle side braking surface may either be formed directly at the housing of the endoscope handle or may be formed at a portion which is non-rotatably coupled to the housing of the endoscope handle such as the shifting element described below. The first shaft side coupling surface and the second shaft side coupling surface may either be formed integrally with the control shaft or may be formed at a portion which is non-rotatably coupled to the control shaft such as the supporting flange described below.

In particular, the first control wheel and the second control wheel are supported to be axially translatable relative to the control shaft and to the housing of the endoscope handle. As such, a shifting element may be used as a plunger element for closing and opening the coupling portions, i.e. pushing the respective coupling surfaces towards each other. In particular, the shifting element further described below may be adapted to activate a rotation of the first control wheel or of the second control wheel via the coupling portions (i.e. connect the control wheels to the control shaft). When switching between the first mode of operation, the neutral state and the second mode of operation, the control wheels are preferably translated in axial direction. In this manner, apart from the shifting element no additional member is necessary for operating the coupling portions. An operation of the coupling portions and the braking portions is thus efficiently and simply achieved.

Preferably, the steering switch mechanism may comprise a manually operable switch input device being provided for receiving an input by a user, and a shifting element being shiftably supported at the housing to be axially shiftable relative to the control shaft and/or relative to the housing of the endoscope handle at least between a first position, in which the first coupling portion is closed and the steering input element is coupled to the first control wheel, and a second position, in which the second coupling portion is closed and the steering input element is coupled to the second control wheel. Preferably such a shifting element is moveable parallel to or along an axis of the control shaft. The shifting element may extend coaxial with or parallel to the axis of the control shaft.

In particular, one among the first coupling portion and the first braking portion may be arranged between or formed by the first control wheel and a non-translatable member (e.g. the supporting flange) which is axially non-translatable with respect to (the housing of) the endoscope handle. The other one among the first coupling portion and the first braking portion may be arranged between or formed by the first control wheel and the shifting element. Especially preferred, one among the second coupling portion and the second braking portion may be arranged between or formed by the second control wheel and the non-translatable member. The other one among the second coupling portion and the second braking portion may be arranged between or formed by the second control wheel and the shifting element. Each control wheel may be arranged between one of the coupling portions and one of the braking portions, optionally forming part of the respective coupling portion and/or braking portion. In particular, each control wheel may be shiftable relative to (the housing of) the endoscope handle.

Thus, on one side of the steering mechanism comprising one of the control wheels (e.g. the first control wheel), when the shifting element (e.g. a member that is non-rotatable with respect to the endoscope handle/the housing thereof) is shifted, the shifting element may be adapted to push against a corresponding one of the control wheels (e.g. the first control wheel) via the coupling or braking portion (e.g. the first braking portion) arranged therebetween, such that said coupling or braking portion is or stays closed. Further, the shifting element may be adapted to push the corresponding control wheel such that the coupling portion or braking portion (e.g. the first coupling portion) arranged between said control wheel and the non-translatable member (e.g. a supporting flange fixed to the control shaft) is or stays opened.

Simultaneously, on another side of the steering mechanism comprising the other one of the control wheels (e.g. the second control wheel), when the shifting element is shifted, at least one of the coupling and braking portions (e.g. the second braking portion) arranged on either side of the corresponding control wheel may be opened. In particular, on the other side of the steering mechanism, the corresponding biasing element may be provided to bias the corresponding control wheel such that it shifts along with/follows the shifting element. Preferably, said control wheel on the other side of the steering mechanism follows the shifting element until it is stopped against and closes the coupling or braking portion (e.g. the second coupling portion) arranged between the said control wheel and the non-translatable member. When the shifting element then moves further, the coupling portion or braking portion (e.g. the second braking portion) arranged between the shifting element and the corresponding control wheel is adapted to open.

In particular, the first braking portion may be formed between the shifting element and the first control wheel and the second braking portion may be formed between the shifting element and the second control wheel. The first biasing element may be accommodated in a space formed between the shifting element and the first control wheel, which provides a particularly compact assembly. Similarly, the second biasing element may be accommodated in a space formed between the shifting element and the second control wheel.

A first distance between the first wheel side coupling surface and the first wheel side braking surface of the first control wheel is preferably shorter than a second distance between the first shaft side coupling surface and the first handle side braking surface in the neutral position (i.e. when the first and second shaft side coupling surfaces are arranged symmetrically with respect to the first and second handle side braking surfaces). A third distance between the second wheel side coupling surface and the second wheel side braking surface of the second control wheel is preferably shorter than a fourth distance between the second shaft side coupling surface and the second handle side braking surface in the neutral position. In this manner, in the neutral position only the braking portions may be closed. Thus, it is possible to bias the control wheels in the automatically closed position when the steering switch mechanism is in the neutral position. Also, this allows the above described stopping of the control wheels against the coupling or braking portion arranged between the control wheels and the non-translatable member.

Further preferably, the shifting element is a cage or casing accommodating the first control wheel and the second control wheel. In this case, the shifting element may protect and support the control shaft and the control wheels on its inside, e.g. forming a pre-assemblable portion. The supporting flange may advantageously be arranged at a central area of the housing of the endoscope handle. Thus, the first control wheel may at least partially be arranged in a first axial space formed between the shifting element and a first supporting flange connected to or integrally formed with the control shaft. Further, the second control wheel may be at least partially arranged in a second axial space formed between the shifting element and the first supporting flange. In particular, the supporting flange is preferably axially non-translatable with respect to the housing of the endoscope handle. In this manner, the control shaft may be non-translatable and rotatable with respect to (the housing of) the endoscope handle and the shifting element may be translatable and non-rotatable with respect to (the housing of) the endoscope handle, such that a particularly stable support of the control shaft and the shifting element in the housing may be achieved.

According to one embodiment, the steering switch mechanism may be actuated via a lever rotatably supported at the endoscope handle, particularly coaxially to the steering input element, and being connected to the shifting element via a transmission structure, preferably including a ramp surface or a threading, to transform a rotational input by the user into an axial shifting of the shifting element. In general, such a lever can be arranged anywhere at an outer side of the housing of the endoscope handle. It is however preferable, if the lever is arranged coaxially or adjacent to/near the steering input element, such that one-hand manipulation is easier for the user. The transmission structure may act to shift the shifting element in both axial directions. Alternatively, the transmission structure may act to shift the shifting element from a starting position (e.g. corresponding to the first or second mode of operation) against the load of an additional spring, with said load being adapted to return the shifting element to the starting position.

According to another embodiment, the steering switch mechanism is actuated via a slider which is slidably supported in (the housing of) the endoscope handle and has two opposing ends which extend from (the housing of) the endoscope handle for receiving the input by the user. The slider may be connected to the shifting element, preferably via transmission rods, for transforming a sliding/shifting movement of the slider into a shifting movement of the shifting element. Preferably, the transmission rods may form part of a transmission device which reduces a force needed to shift the shifting element. For example, the transmission rods may be correspondingly connected to hinges between links of a chain. The chain may have two ends connected to the shifting element at axially spaced positions. Further, the chain is preferably longer than the distance between the axially spaced positions, such that the links of the chain follow a zigzag-course between the axially spaced positions. Thus, a pressure against hinges between the links may result in an alignment of the adjacent links, lengthening a corresponding portion of the chain, and a pulling at said hinges may result in a smaller angle between said links, shortening a corresponding portion of the chain. In particular, there is respectively one link of the chain between each of the transmission rod and the shifting element and two links between the two transmission rods. Thus, shifting the switch input element may result in pushing one transmission rod towards the shifting element, in particular aligning the respectively adjacent links, and pulling the other transmission rod from the shifting element, in particular reducing an angle between the respectively adjacent links. Thus, one portion of the chain is lengthened and another portion of the chain is shortened, which is translated into a shifting movement of the shifting element. Alternatively, the slider may e.g. be connected or fixed directly to the shifting element or form part of the shifting element. In this case, shifting the slider would result directly in a shifting of the shifting element.

According to another alternative embodiment, the steering switch mechanism may be actuated via the steering input element, with the steering input element being supported to be axially translatable relative to the housing of the endoscope handle and being integrally formed with or connected to the shifting element in order to transform a translational movement of the steering input element into a shifting movement of the shifting element. That is, the steering input element may serve as a switch input element. In this manner, the control wheels may be controlled via a rotational input into the steering input element and the steering switch mechanism may be controlled via a translatory input into the steering input element. For example, the steering input element and the control shaft may serve as the shifting element, optionally being integrally formed with each other, and braking portions may be arranged directly at or formed integrally with the housing of the endoscope handle (i.e. a non-shiftable cage or the like is required). Alternatively, the steering input element may be axially translatably and non-rotatably mounted on the control shaft and may be non-translatably and rotatably connected to the shifting element (e.g. formed as the cage or casing). Thus, an axial translation of the steering input element may be transmitted to the shifting element without moving the control shaft (at least portions thereof forming the first and second shaft side coupling surfaces).

The endoscope according to the disclosure may be a two-way-bendable endoscope with one steering wire being attached to each of the two control wheels. Alternatively, the endoscope may be a four-way-bendable endoscope, with each of the control wheels being connected to a pair of steering wires which are moved in opposite directions when driven by the corresponding control wheel.

Further alternatively, the endoscope may be a four-way-bendable endoscope with a three-wire-steering arrangement, wherein the endoscope may have (exactly) three steering wires, namely the first steering wire, the second steering wire and a third steering wire, which may each be radially spaced from an insertion cord axis and may be angularly spaced with respect to each other in the circumferential direction of the insertion cord. A proximal end portion of the first steering wire may be connected to a first wheel portion of the first control wheel to bend the bending section in a first bending direction. A proximal end portion of the second steering wire may be connected to a third wheel portion of the second control wheel to bend the bending section in a second bending direction. Further preferably, a proximal end portion of the third steering wire may be connected to the first control wheel via a connecting wire to bend the bending section in a third bending direction and may further be connected to the second control wheel via said connecting wire to bend the bending section in a fourth bending direction. The connecting wire may have a first end connected to a second wheel portion of the first control wheel and be adapted to be wound thereon in a direction opposite to the first steering wire. A second end of the connecting wire may be connected to a fourth wheel portion of the second control wheel and be adapted to be wound thereon in a direction opposite to the second steering wire. An intermediate portion of the connecting wire may be guided through or around (i.e. redirected by) a redirecting member, e.g. a passive drum or a sliding member, which may be translatable along (a central axis of) the connecting wire.

Regarding further information about the above described three-wire-steering arrangement including the three wires, particularly an arrangement and dimensioning/radiuses of the first wheel portion, the second wheel portion, the third wheel portion and the fourth wheel portion, DE 10 2021 116162.2 is referred to, which is incorporated herein by reference. The above described three-wire-steering arrangement can advantageously be used with the endoscope according to the present disclosure, since the steering switch mechanism of said endoscope may serve as a braking or locking mechanism to uncouple a rotation of the first control wheel and a rotation of the second control wheel from each other. I.e. unwanted interaction of control of the first and third bending directions with control of the second and fourth bending directions due to a torque or force transmitted between the first and second control wheels via the connecting wire is minimized or even avoided. Accordingly, a definite, accurate control of the three-wire-steering arrangement is possible. Additionally, little construction/assembly space within the endoscope handle and/or within the insertion cord is required and weight of the endoscope can be reduced.

Preferably the endoscope is a single use endoscope, meaning that the endoscope is optimized for single use, e.g. in that it is preferably made of limited number of elements to be assembled, as this will lower the cost of assembly, which is a relatively large proportion of the total cost of the endoscope. This also means that parts of the endoscope preferably are made up by a limited number of elements, and with focus on ease of assembly, and in materials that enable the parts to be made at low cost, e.g. by plastic moulding. This compared to traditional reusable endoscopes, where focus is to provide endoscopes, which must be able to withstand the rather aggressive cleaning processes and general harsh handling over time.

Further, the object may be achieved by a system comprising an endoscope as described above and a monitor connectable to the endoscope.

BRIEF DESCRIPTION OF FIGURES

The following figures illustrate exemplary embodiments of the disclosure. The disclosure is not limited to the embodiments described below. Other embodiments, combinations of embodiments and modifications may be provided within the scope of protection defined by the claims.

DETAILED DESCRIPTION

Figures 1, 2:
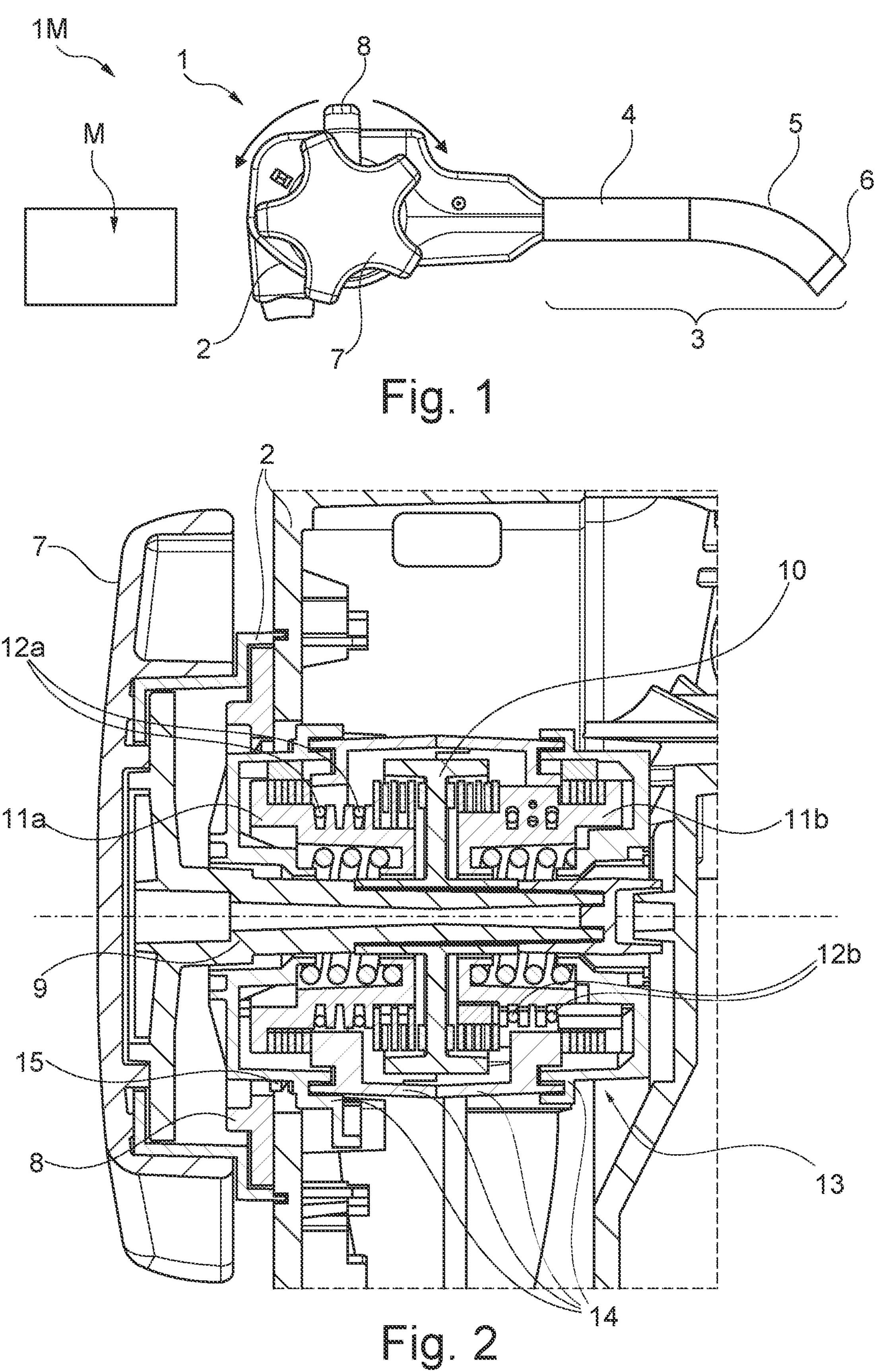
FIG. 1 shows a schematic view of a system comprising an endoscope and a monitor according to the present disclosure.
FIG. 2 shows a partial cross-sectional view of the endoscope according to FIG. 1.

FIG. 1 shows a schematic view of an endoscopic system 1M including an endoscope 1, which is preferably a single-use endoscope, and a monitor M. The endoscope 1 has a proximal endoscope handle 2 and an insertion cord 3 extending distally from the endoscope handle 2. The insertion cord 3 has an insertion tube 4 connected to the endoscope handle 2. The insertion cord 3 further includes a bending section 5 connected to a distal end of the insertion tube 4 and a distal tip unit 6 connected to a distal end of the bending section 5. The bending section 5 is configured to perform a bending/pivoting/swivelling movement in four different directions/in two bending planes, preferably with orthogonal angles between circumferentially adjacent directions. This enables a steering of the endoscope 1. In a neutral state, the bending section 5 is unbent by the steering mechanism, preferably straight/in alignment with the insertion tube 4.

The bending/pivoting/swivelling movement is controlled by a steering mechanism including a steering input element 7, particularly a hand wheel. Further, the steering mechanism includes a switch input element 8, which is exemplarily formed as a lever in the embodiment shown in FIG. 1 and which is adapted to switch between a first mode of operation for bending the bending section 5 in a first bending plane and a second mode of operation for bending the bending section 5 in a second bending plane as well as a neutral state in which bending in both directions is braked/prevented/not possible. The steering input element 7 and the switch input element 8, also referred to as the steering wheel 7 and the switch lever 9, are provided at an outer side of a housing of the handle 2 and are supported at the handle 2 to be rotatable coaxially with respect to each other. In FIG. 1, the switch input element 8 is shown in a neutral position corresponding to the neutral state and can be operated/rotated as indicated by arrows in clockwise or anti-clockwise direction in order to switch from the neutral state into the first mode of operation or into the second mode of operation.

The distal tip unit 6, also referred to as the distal tip 6, comprises a peripheral wall defining a cavity housing image capturing means, such as a miniature video camera, and illuminating means, such as light-emitting diodes or optical fibers connected to a proximal source of light. The illuminating means and/or image capturing means are provided to illuminate and inspected the patient's body cavity. An image captured by the image capturing means can be shown on the monitor M. The monitor M is provided separately from and connectable with the endoscope 1.

A positioning interface, or interface, functions to control the position of the insertion cord. The handle 2 is an example of a positioning interface and, unless stated otherwise, the terms are used interchangeably. The positioning interface also functions to provide the steering controls, e.g. knobs, levers, buttons, and the like, to steer the field of view of the camera and the elevator controls. Alternatively, a different positioning interface can be provided that is connected to the insertion cord and is detachably connected to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

In some embodiments, the monitor M is operable to receive image data, present a graphical user interface to allow a user to manipulate image data with a touch screen, and, optionally, output a video signal to allow remote viewing of the images presented with the touch screen. A separate, potentially remote, display screen may be connected to the monitor M to present the images. Alternatively or additionally, the monitor M may comprise a housing supporting an integrated display screen.

The MONITOR M includes a circuit board interconnecting a processor, a memory including graphical user interface (GUI) logic, and a field-programmable gate array (FPGA), which are collectively referred to as a video processing circuit. The MONITOR M may also include a microphone, a wireless interface operable to receive user inputs via a mouse, keyboard, or other physical user input devices. Example wireless interfaces include Bluetooth and Zigbee controllers. A user interface may also comprise a USB port to receive a USB connector of a wired user input device. Thus, the MONITOR M provides for flexibility in receiving user inputs via various user input devices. The circuit board may comprise one or more rigid circuit board parts provided to mount some or all of the electronic devices, including the processor and the FPGA. The memory may also be mounted thereon, for example.

The FPGA is optionally provided because it is capable of rapid power-up (i.e. short boot-up time) and thus is useful in emergency situations. FPGAs process data very fast compared to other memory/instruction combinations and are re-programmable. Therefore, FPGAs facilitate presentation of a live view of the images captured by the endoscope in real-time with minimal latency so that the physician observing the live view can take immediate actions even in emergency situations. The processor combines images from the endoscope with the GUI and provides the combined data to the FPGA to be output. In a variation of the present embodiment, the functionality of the FPGA may be performed by the processor 50 and the FPGA may be omitted. The MONITOR M is therefore not limited to the precise packaged integrated circuits described herein but can be constructed to take advantage of design and cost targets and future video processing technologies. For example, faster/more costly memory may be used to increase graphics processing speed. Graphics processing may be provided in the FPGA or a processor that incorporates graphics processing logic such as a GPU may be used instead.

The processor may comprise one or more physical processors and/or may be comprised by a plurality of individual processing units. The processor may be a central processing unit (CPU), a graphics processing unit (GPU), a microcontroller unit (MCU), the FPGA, or any combination thereof.

The memory may comprise multiple interconnected circuits, including a memory circuit embedded in the processor, a memory integrated circuit connected to the processor, a hard-drive connected to the processor, and any other devices operable to store data and communicate with the processor and/or the FPGA.

The term "logic" as used herein includes software and/or firmware executing on one or more programmable processing devices, application-specific integrated circuits, field-programmable gate arrays, digital signal processors, hard-wired logic, or combinations thereof. Therefore, in accordance with the embodiments, various logic may be implemented in any appropriate fashion and would remain in accordance with the embodiments herein disclosed. Logic may comprise processing instructions embedded in non-transitory machine-readable media (e.g. memory).

The GUI logic comprises processing instructions to generate a GUI presented with or by the MONITOR M. The GUI can be responsive to user inputs received via the touch screen or other user inputs. The processor receives image data from the medical device interfaces and outputs video signals incorporating the GUI and image data. Image data may be referred to "live images" or "live video" if they are received substantially in real-time from the endoscopes. The video signals may be received by a memory buffer and the buffer may be read by the display module or video output card to present the GUI and images. Techniques for presenting images are well known, including techniques using buffers or mapped memory. The GUI may comprise first and second panels provided side-by-side in a view. The second panel presents live images and is positioned on the right side of the view, with the first panel positioned on the left side of the view. The GUI may present in the first panel a small version of live images provided by a second endoscope and the user may use the GUI to switch the live images from the first and second endoscopes so that the images from the second endoscope are presented in the second panel while the images from the first endoscope are reduced and presented in the first panel. However, the views from the different endoscopes can be selected by the user with the GUI for presentation in the first or second panel or not displayed at all. The GUI may present various icons corresponding to actions selectable by the user with any of the above-described user input devices, to for example store a copy of a live image, store a portion of video corresponding to live images, invert the views, apply correction curves to the image data to reduce overexposure, etc.

FIG. 2 shows a partial cross-sectional view of the endoscope 1 according to FIG. 1 illustrating the steering mechanism. A control shaft 9 is rotatably supported in the housing of the endoscope handle 2. One axial end of the control shaft 9 protrudes from the housing and is fixedly connected to the steering input element 7. Further, a supporting flange 10 is fixedly mounted on the control shaft 9, particularly on a central area thereof in the axial direction. On one axial side of the supporting flange 10, a first control wheel **11*a* is arranged to be axially translatable with respect to the control shaft 9 and to be rotatable together with the control shaft 9. A first steering wire or a pair of first steering wires 12*a* are wound around the first control wheel 11*a* and are adapted to transfer a rotation of the first control wheel 11*a* to the bending section 5 to bend the bending section 5 in the first bending plane. On another axial side of the supporting flange 10, a second control wheel 11*b* is arranged to be axially translatable with respect to the control shaft 9 and to be rotatable together with the control shaft 9. A second steering wire or a pair of second steering wires 12*b* are wound around the second control wheel 11*b* and are adapted to transfer a rotation of the second control wheel 11*b* to the bending section 5 to bend the bending section 5** in the second bending plane.

The first steering wire or pair of first steering wires **12*a* and the second steering wire or pair of second steering wires 12*b*** extend from the handle through the insertion tube and the bending section and are connected to the distal end of the bending section or the tip part to effect bending of the bending section when tensioned. In one variation, the pair of steering wires are portions of a single wire and are connected to each other by an intermediate portion, or wire loop (not shown), connected to the distal tip and/or the distal end of the bending section. In another variation, the steering wires are separate wires, each having a distal portion connected to the bending section and/or the distal tip part.

The control shaft 9 is selectively engageable to the first control wheel **11*a* and to the second control wheel 11*b* via a steering switch mechanism 13 which is explained in more detail below with reference to FIGS. 2 to 5C. Said steering switch mechanism 13 includes a shifting element 14, which is axially translatable relative to the housing of the endoscope handle 2 and the control shaft 2. The shifting element 14, exemplarily, has four parts forming a cage or casing which accommodates the control shaft 9 and the first and second control wheels 11***a*, 11*b*. In particular, the first control wheel 11*a* is accommodated in a first axial space formed between the shifting element 14 and the supporting flange 10 on the one axial side and the second control wheel 11*b* is accommodated in a second axial space formed between the shifting element 14 and the supporting flange 10 on the other axial side.

At an axial end portion next to/close to the steering input element 7, the shifting element 14 forms a transmission structure 15. The transmission structure 15 protrudes radially outwards from the cage and forms a ramp surface which faces towards the control knob 7 and extends both circumferentially and axially. The switch input element 8 is rotatably supported at the endoscope handle 2 so as to be rotatable coaxially with the steering input element 7. The switch input element 8 is adapted to press against the ramp surface of the transmission structure 15, such that a rotation of the switch input element 8 is transformed into a translational movement of the shifting element 14.

Figure 3:
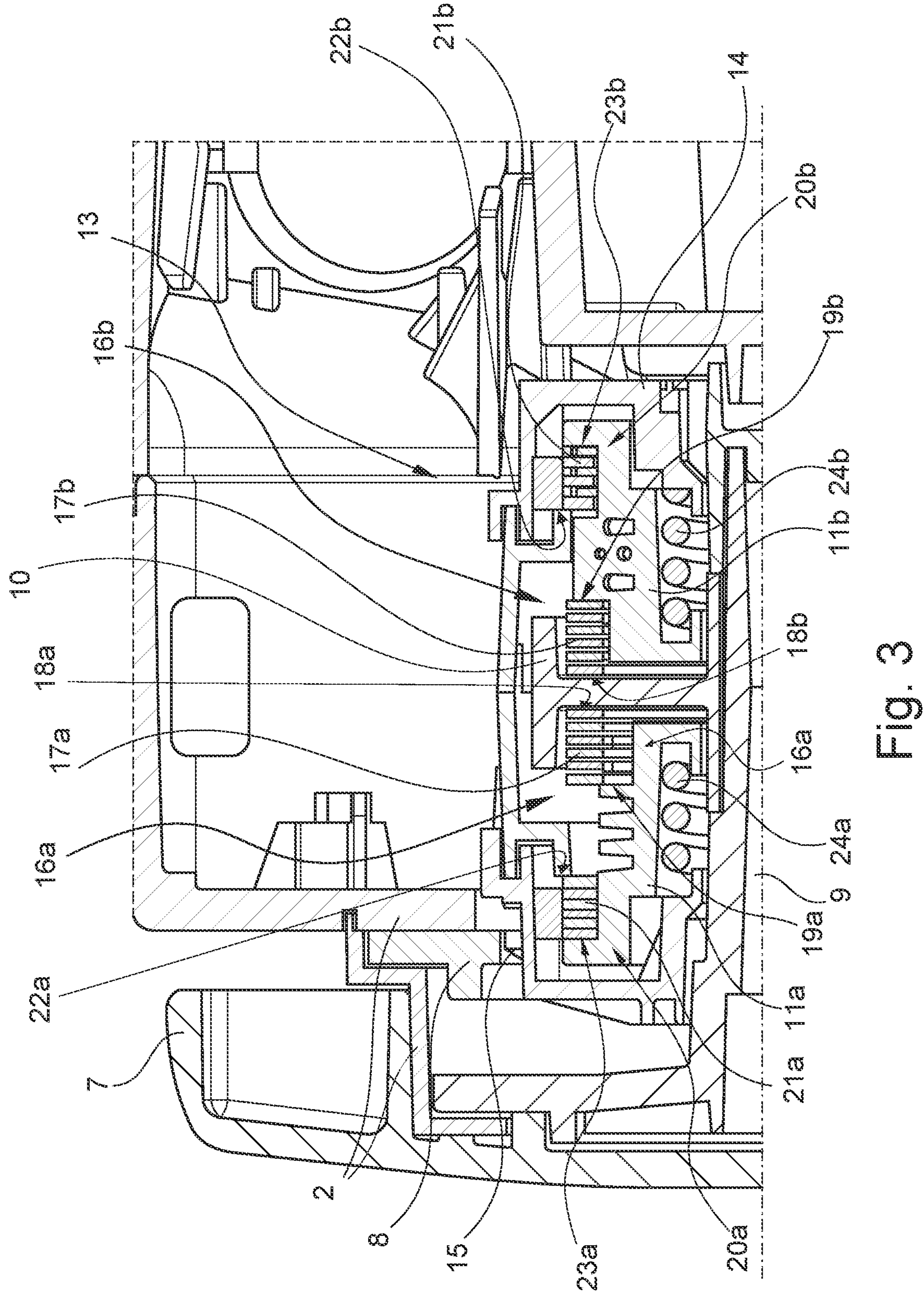
FIG. 3 shows a partial sectional view of a steering mechanism of the endoscope according to FIGS. 1 and 2 in a neutral state.
Figure 4:
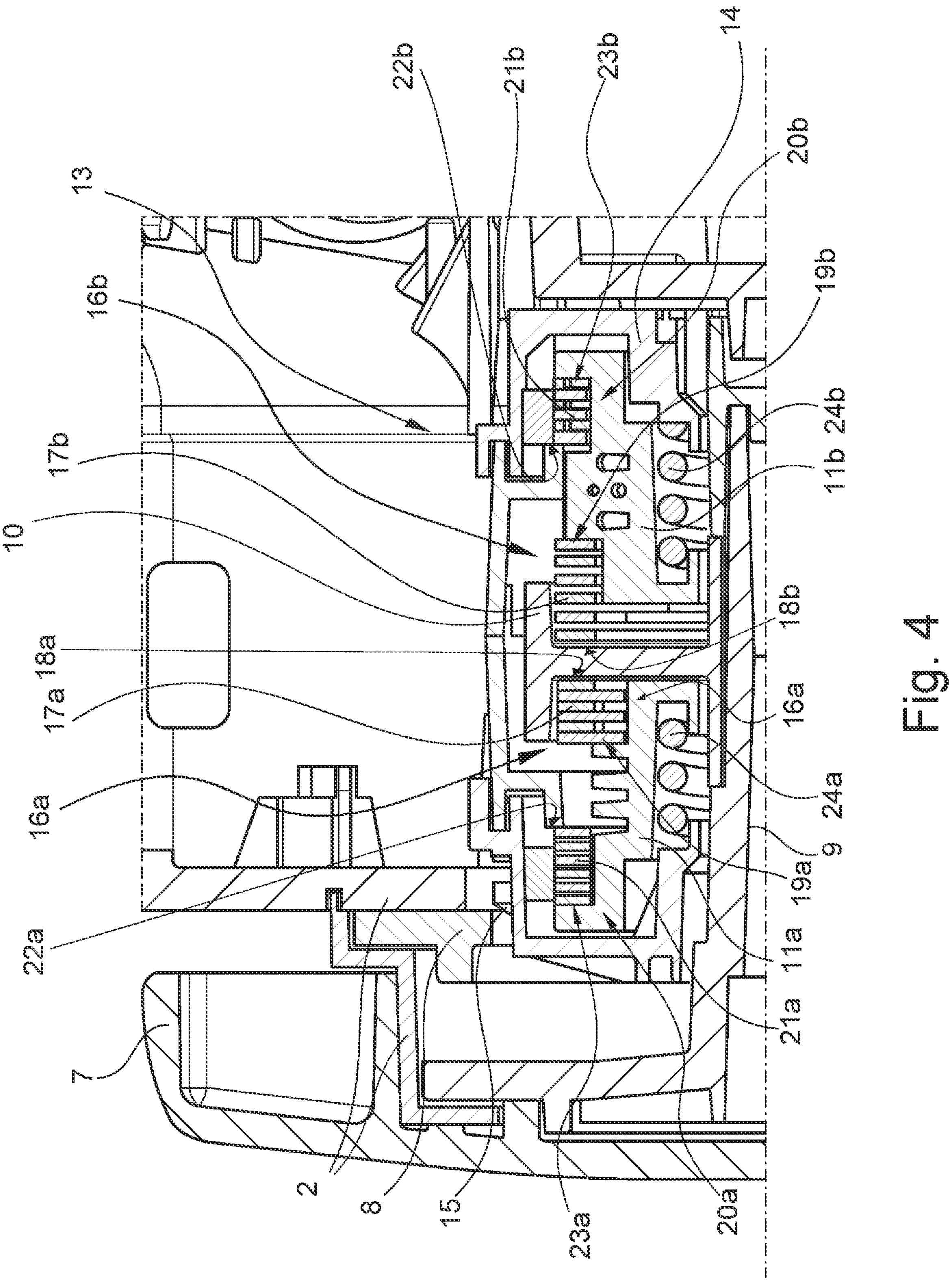
FIG. 4 shows a partial sectional view of a steering mechanism of the endoscope according to FIGS. 1 and 2 in one mode of operation.

FIGS. 3 and 4 show a partial sectional view of the endoscope of FIGS. 1 and 2, illustrating the steering mechanism and the steering switch mechanism in detail.

As can be seen in FIG. 3, the steering switch mechanism 13 includes a first coupling portion 16*a* comprising a first friction fit arrangement 17*a*, in this embodiment a first stack of friction discs, arranged between the first control wheel 11*a* and the supporting flange 10. The friction discs of the first friction fit arrangement 17*a* are alternatingly non-rotatably supported at the supporting flange 10 or at the first control wheel 11*a*. In the axial direction, the first friction fit arrangement 17*a* is arranged between a first shaft side coupling surface 18*a* formed on the supporting flange 10 and a first wheel side coupling surface 19*a* formed on the first control wheel 11*a*. Further, the steering switch mechanism 13 includes a second coupling portion 16*b* comprising a second friction fit arrangement 17*b*, in this embodiment a second stack of friction discs, arranged between the second control wheel 11*b* and the supporting flange 10. The friction discs of the second friction fit arrangement 17*b* are alternatingly non-rotatably supported at the supporting flange 10 or at the second control wheel 11*b*. In the axial direction, the second friction fit arrangement 17*b* is arranged between a second shaft side coupling surface 18*b* formed at the supporting flange 10 and a second wheel side coupling surface 19*b* formed at the second control wheel 11*b*.

Moreover, the steering switch mechanism 13 includes a first braking portion 20*a* comprising a third friction fit arrangement 21*a*, in this embodiment a third stack of friction discs, arranged between the first control wheel 11*a* and the shifting element 14. The friction discs of the third friction fit arrangement 21*a* are alternatingly non-rotatably supported at the shifting element 14 or at the first control wheel 11*a*. In the axial direction, the third friction fit arrangement 21*a* is arranged between a first handle side braking surface 22*a* formed at the shifting element 14 and a first wheel side braking surface 23*a* formed at the first control wheel 11*a*. Further, the steering switch mechanism 13 includes a second braking portion 20*b* comprising a fourth friction fit arrangement 21*b*, in this embodiment a fourth stack of friction discs, arranged between the second control wheel 11*b* and the shifting element 14. The friction discs of the fourth friction fit arrangement 21*b* are alternatingly non-rotatably supported at the shifting element 14 or at the second control wheel 11*b*. In the axial direction, the fourth friction fit arrangement 21*b* is arranged between a second handle side braking surface 22*b* formed at the shifting element 14 and a second wheel side braking surface 23*b* formed at the second control wheel 11*b*.

The first and second wheel side coupling surfaces 19*a*, 19*b* and the first and second wheel side braking surfaces 23*a*, 23*b* respectively face towards the supporting flange 10. The first and second shaft side coupling surfaces 18*a*, 18*b* and the first and second handle side braking surfaces 22*a*, 22*b* correspondingly face in an opposite direction. A first compression spring as a first biasing element 24*a* is arranged between the first control wheel 11*a* and the shifting element 14. A second compression spring as a second biasing element 24*b* is arranged between the second control wheel 11*b* and the shifting element 14. Thus, the first and second biasing elements 24*a*, 24*b* respectively bias the first and second control wheels 11*a*, 11*b* towards the supporting flange 10, i.e. bias the first and second coupling portions 16*a*, 16*b* and the first and second braking portions 20*a*, 20*b* towards a closed state.

In the following, an operation of the steering switch mechanism, i.e. a switching from a neutral state (FIG. 3) to a first operating state corresponding to the first mode of operation (FIG. 4) is described with reference to FIGS. 3 to 5C. It should be noted, that a switching from the neutral state to a second operating state/second mode of operation is essentially symmetrical thereto (i.e. in the description text, reference sign portions "a" and "b" are essentially exchangeable).

In the neutral state shown in FIG. 3, the shifting element 14 is arranged in such a manner that the supporting flange 10 is arranged centrally in the shifting element 14 and the first and second control wheels 11*a*, 11*b* are arranged symmetrically with respect to the supporting flange 10. A first distance between the first wheel side coupling surface 19*a* and the first wheel side braking surface 23*a* of the first control wheel 11*a* is shorter than a second distance between the first shaft side coupling surface 18*a* and the first handle side braking surface 22*a*. A third distance between the second wheel side coupling surface 19*b* and the second wheel side braking surface 23*b* of the second control wheel 11*b* is shorter than a fourth distance between the second shaft side coupling surface 18*b* and the second handle side braking surface 22*b*. Thus, the first and second control wheels 11*a*, 11*b* are dimensioned such that, in the neutral state, the first and second braking portions 20*a*, 20*b* are closed (i.e. the third and fourth friction fit arrangements 21*a*, 21*b* are pushed together) by the first and second biasing elements 24*a*, 24*b*. Accordingly, the first and second control wheels 11*a*, 11*b* are held non-rotatably relative to the housing of the endoscope handle 2 via the shifting element 14 and the first and second braking portions 20*a*, 20*b*.

Since the first and second braking portions 20*a*, 20*b* provide a stop against further movement of the first and second control wheels 11*a*, 11*b* due to the first and second biasing elements 24*a*, 24*b*, the first and second coupling portions 16*a*, 16*b* are open (i.e. the first and second friction fit arrangements 17*a*, 17*b* are not pressed together/have play/form at least one axial clearance). That is, no force is transmitted from the steering input wheel 7 via the control shaft 9 and the supporting flange 10 to the first and second control wheels 11*a*, 11*b*. Accordingly, in the neutral state, the first and second control wheels 11*a*, 11*b* do not rotate, the first and second steering wire(s) 12*a*, 12*b* are not actuated and the bending section 5 is not operated.

When the switch input element 8 is operated by a user starting from the neutral state in one direction, e.g. clockwise in top view, the switch input element 8 acts on the ramp surface of the transmission structure 15, such that the shifting element 14 is pushed in an axial direction, in this example in a direction away from the steering input wheel 7. Thus, via the closed second braking portion 20*b*, the second control wheel 11*b* is pushed by the shifting element 14 and the second braking portion 20*b* stays closed. The second coupling portion 16*b* opens further. Thus, the second control wheel 11*b* continues to be braked and non-operated via the control shaft 9. Accordingly, the second steering wire(s) 12*b* is/are not operated and no bending of the bending section 5 in the second bending plane is possible.

Simultaneously, the first control wheel 11*a* is pushed towards the supporting flange 10 by the shifting element 14 via the first biasing element 24*a*. The first biasing element 24*a* is compressed. Once the first wheel side coupling surface 19*a* and the first shaft side coupling surface 18*a* start to compress the first friction fit arrangement 17*a* of the first coupling section 16*a*, the third friction fit arrangement 21*a* of the first braking portion 20*a* starts to loosen. This corresponds to a transitional state of the steering mechanism and the steering switch mechanism 13.

When the switch input element 8 is operated further by the user in the one direction, the first friction fit arrangement 17*a* is further compressed. Simultaneously, the first wheel side braking surface 23*a* and the first handle side braking surface 22*a* move further apart, thus loosening their connection and opening the first braking portion 20*a*, as shown in FIG. 4. Thus, the first control wheel 11*a* is rotationally disconnected from the housing of the endoscope handle 2 and connected to the control shaft 9 and the steering input element 7. Accordingly, a user input at the steering input element 7 can now be transmitted to the bending section 5 via the first coupling portion 16*a*, the first control wheel 11*a* and the first steering wire(s) 12*a* to bend the bending section 5 in the first bending plane. This corresponds to the first mode of operation.

When the switch input element 8 is operated in the other direction, e.g. counterclockwise in the top view, starting from the first mode of operation, the shifting element 13 is moved towards the steering input element 7. Thus, the third friction fit arrangement 21*a* is compressed and the first friction fit arrangement 17*a* is loosened, closing the first braking portion 20*a* and opening the first coupling portion 16*a*. Thus, the first control wheel 11*a* is rotationally connected to the housing of the endoscope handle 2 and disconnected from the control shaft 9 and the steering input element 7. Simultaneously, the second control wheel 11*b* is pushed towards the supporting flange 10 by the shifting element 14 via the second biasing element 24*b*, i.e. follows the shifting element 14, keeping the second braking portion 20*b* closed. Thus, the above described neutral state shown in FIG. 3 is reached, in which the first and second coupling portions 16*a*, 16*b* are open and the first and second braking portions 20*a*, 20*b* are closed, such that both control wheels 11*a*, 11*b* are braked.

When the switch input element 8 is further operated in the other direction, e.g. counterclockwise in the top view, starting from the neutral state shown in FIG. 3, the switch input element 8 acts on the ramp surface of the transmission structure 15, such that the shifting element 14 is pushed (via the transmission structure 15 or via an additional spring not shown in this view) in another axial direction, in this example in a direction towards the steering input wheel 7. Thus, via the closed first braking portion 20*a*, the first control wheel 11*a* is pushed by the shifting element 14 and the first braking portion 20*a* stays closed. The first coupling portion 16*a* opens further. Thus, the first control wheel 11*a* continues to be braked and non-operated via the control shaft 9. Accordingly, the first steering wire(s) 12*a* is/are not operated and no bending of the bending section 5 in the first bending plane is possible.

Simultaneously, the second control wheel 11*b* is pushed towards the supporting flange 10 by the shifting element 14 via the second biasing element 24*b*. The second biasing element 24*b* is compressed. Once the second wheel side coupling surface 19*b* and the second shaft side coupling surface 18*b* start to compress the second friction fit arrangement 17*b* of the second coupling portion 16*b*, the third friction fit arrangement 21*b* of the second braking portion 20*b* starts to loosen. This corresponds to a transitional state of the steering mechanism and the steering switch mechanism 13.

When the switch input element 8 is operated further by the user in the other direction (i.e. counterclockwise in the top view), the second friction fit arrangement 17*b* is further compressed. Simultaneously, the second wheel side braking surface 23*b* and the second handle side braking surface 22*b* move further apart, thus loosening their connection and opening the second braking portion 20*b*. Thus, the second control wheel 11*b* is rotationally disconnected from the housing of the endoscope handle 2 and connected to the control shaft 9 and the steering input element 7. Accordingly, a user input at the steering input element 7 can now be transmitted to the bending section 5 via the second coupling portion 16*b*, the second control wheel 11*b* and the second steering wire(s) 12*b* to bend the bending section 5 in the second bending plane.

Figures 5A, 5B, 5C:
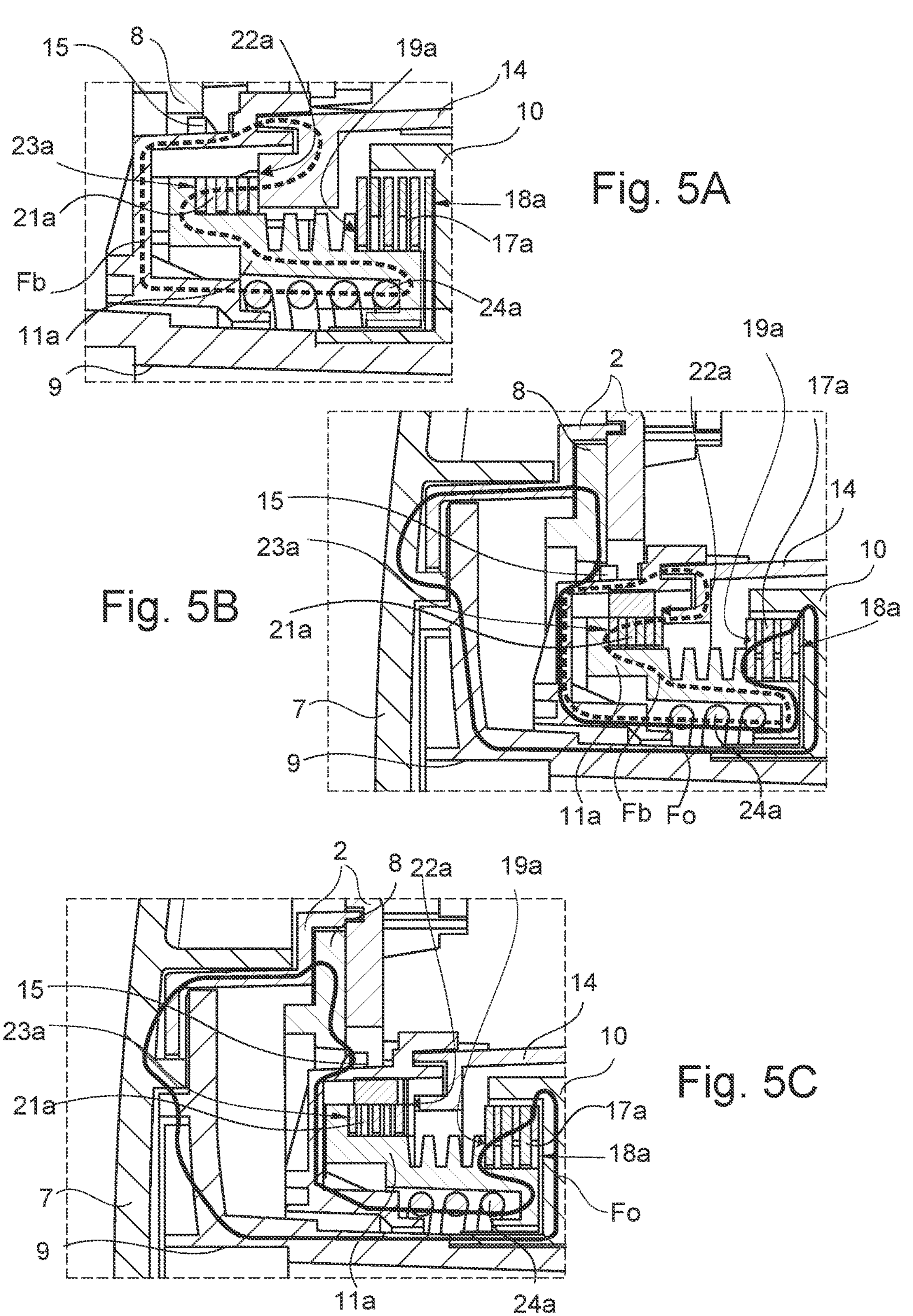
FIGS. 5A. 5B and 5C illustrate force flows in the steering mechanism of the endoscope according to FIGS. 1 to 4, respectively in the neutral state, a transitional state and an operating state corresponding to a first mode of operation.

FIGS. 5A, 5B and 5C respectively illustrate force flows in the steering mechanism of FIGS. 1 to 4, with FIG. 5A showing a braking force flow Fb, FIG. 5B showing the braking force flow Fb and an operating force flow Fo in the transitional state and FIG. 5C showing the operating force flow Fo in a first operating state corresponding to the first mode of operation. Exemplarily, only the one side of said steering mechanism is shown.

In detail, in the neutral state shown in FIG. 5A, there is an axial clearance in the first friction fit arrangement 17*a* of the first coupling portion 16*a* and no force is transmitted between the control shaft 9 and the first control wheel 11*a*. Further, a braking force flow Fb (dashed line in FIGS. 5A and 5B) runs from the shifting element 14 through the third friction fit arrangement 21*a* to the first control wheel 11*a*. From there, the braking force flow Fb further runs through the second biasing element 24*b* back into the shifting element 14, closing a corresponding force flow circuit. Although only the one side of said steering mechanism is shown, the other side thereof including the second control wheel 11*b* is in a similar state.

FIG. 5B illustrates force flows in the steering mechanism of FIG. 3 in the transitional state. A braking force flow Fb as described with reference to FIG. 5A runs through the third friction fit arrangement 21*a*. Further, an operating force flow Fo (continuous line in FIGS. 5B and 5C) runs from the steering input element 7 through the control shaft 9, the supporting flange 10 and the first friction fit arrangement 17*a* to the first control wheel 11*a*. From there, the operating force flow Fo further runs through the first biasing element 24*a*, the shifting element 14, the transmission structure 15, the switch input element 8, a housing portion of the endoscope handle 2 accommodating the switch input element 8, and back into the steering input element 7, closing a corresponding force flow circuit. Although only the one side of said steering mechanism is shown, force flow in the other side including the second control wheel 11*b* is similar to the one shown in FIG. 5A.

In the first operating state shown in FIG. 5C, there is an axial clearance in the third friction fit arrangement 21*a* of the first braking portion 20*a* and no force is transmitted between the shifting element 14 and the first control wheel 11*a*. Further, the operating force flow Fo (continuous line in FIGS. 5A and 5B) as described with reference to FIG. 5B circles between the steering input element 7 and the second control wheel 11*b*. Although only the one side of said steering mechanism is shown, force flow in the other side including the second control wheel 11*b* is similar to the one shown in FIG. 5A.

Figures 6A, 6B, 6C:
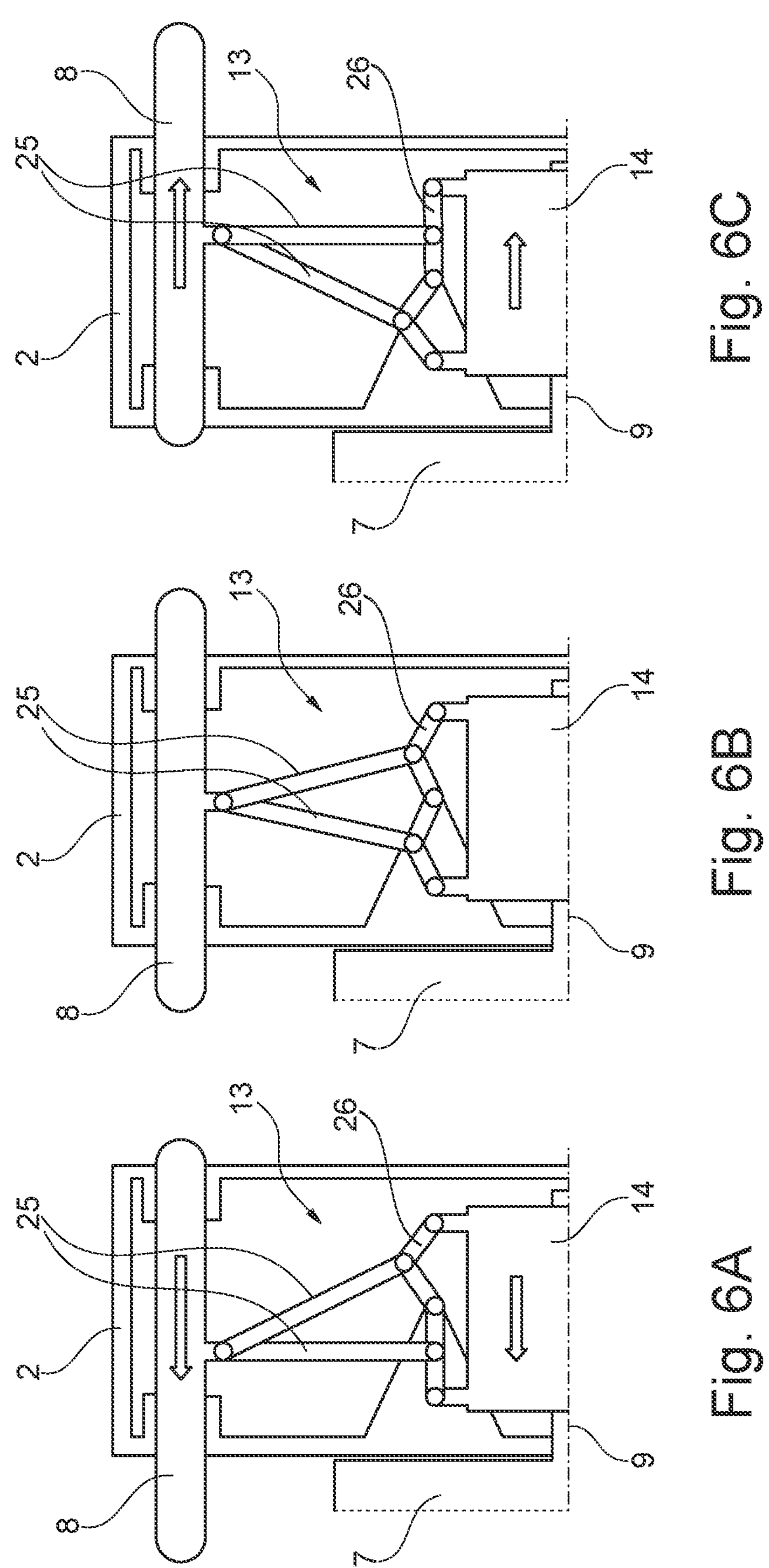
FIGS. 6A[[to 6B]], 6B and 6C schematically illustrate a second embodiment of the endoscope according to the present disclosure.

FIGS. 6A to 6C schematically illustrate a second embodiment of the endoscope 1 according to the present disclosure. Therein, FIG. 6B shows the steering mechanism in the neutral state, whereas FIG. 6C shows the steering mechanism in a first operating state and FIG. 6A shows the steering mechanism in a second operating state. The endoscope 1 is essentially the same as the one described with reference to FIGS. 1 to 5C except for the following differences, particularly relating to the switch input element.

The switch input element 8, e.g. formed as a pin or slider, extends through the endoscope handle 2 and protrudes on both axial ends from the housing of the endoscope handle 2, forming two push buttons for receiving an input by the user. In a central area, the switch input element 8 forms a hinge connecting the switch input element 8 to one end of two transmission rods 25 which are angled with respect to each other. At their respective other ends, each of the transmission rods 25 is further linked to a chain 26. Said chain 26 includes two end link elements and two middle link elements, which are subsequently hinged to each other via a first chain hinge, a second chain hinge and a third chain hinge. One of the two end link elements of the chain 26 connects the shifting element 14 at a first linking position to the other end of one of the transmission rods 25. Another end link element of the chain 26 connects the shifting element 14 at a second linking position to the other end of the other one of the transmission rods 25. The first linking position and the second linking position are axially spaced from each other. The one of the transmission rods 26 is hinged to the first chain hinge and the other one of the transmission rods 26 is hinged to the third chain hinge.

In the neutral state as shown in FIG. 6B, the link elements of the chain 26 form a zigzag-shape or M-like shape. In particular, the transmission rods 25 and the link elements of the chain 26 are symmetrical with respect to a cross-sectional plane of the steering mechanism and the steering switch mechanism 13. When the switch input element 8 is pushed to the one side, as shown in FIG. 6A (or to the other side, as shown in FIG. 6C), the one of the transmission rods 25 pushes the first chain hinge (or the third chain hinge, see FIG. 6C) towards the shifting element 14, preferably aligning the respectively adjacent link elements with respect to each other. The other one of the transmission rods 25 pulls the third chain hinge (or the first chain hinge, see FIG. 6C) away from the shifting element 14. Due to this, the shifting element 14 is pushed in the same direction as the switch input element 8. Then, the shifting element 14 acts on the other components of the steering mechanism in accordance with the first embodiment shown in FIGS. 1 to 5C.

Figure 7:
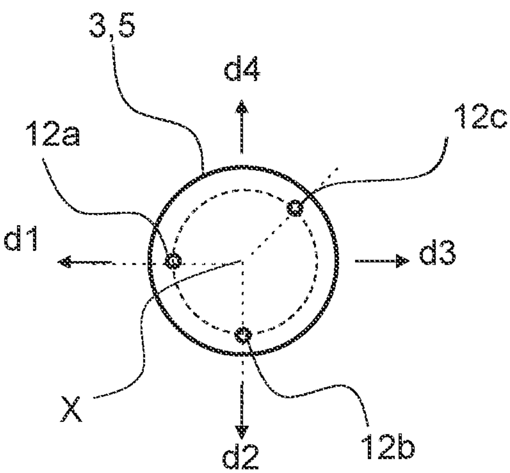
FIG. 7 schematically illustrates a cross-sectional view of an insertion cord of an endoscope including a three-wire-steering arrangement according to a modification of the first or second embodiment.
Figure 8:
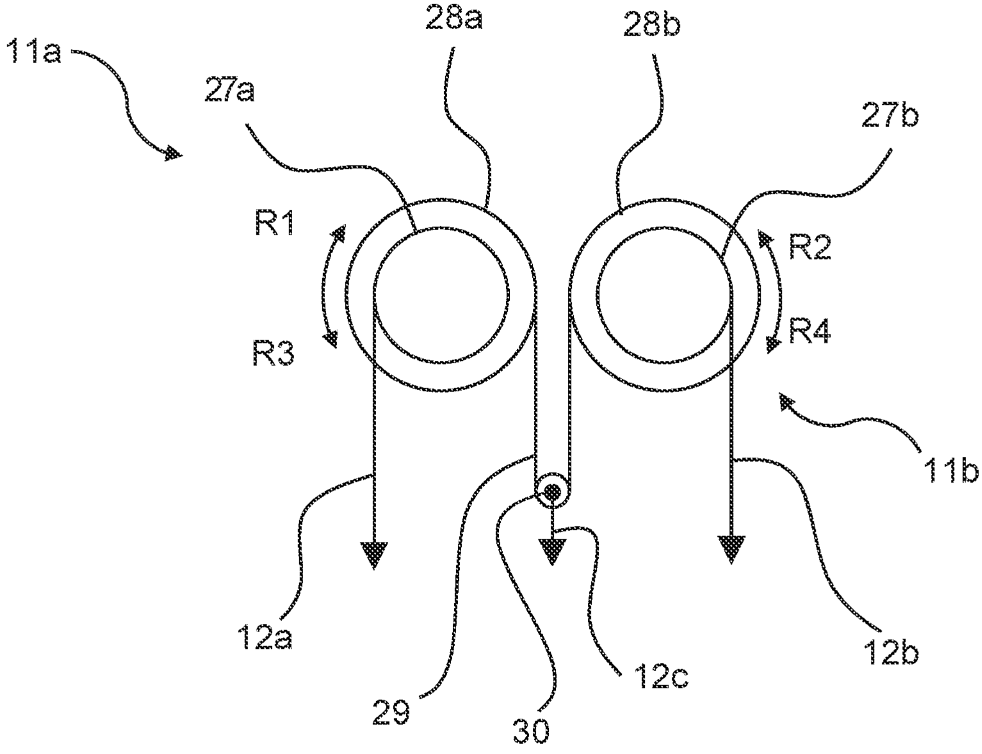
FIG. 8 schematically shows a functioning principle of the three-wire-steering arrangement according to the modification shown in FIG. 7.

FIGS. 7 and 8 illustrate a preferred modification of the first and second embodiments described above including a three-wire-steering arrangement. FIG. 7 schematically shows a cross-sectional view of the insertion cord 3 (e.g. a bending section 5). Therein, the first steering wire 12*a*, the second steering wire 12*b* and a third steering wire 12*c* are arranged at an equal distance from a central axis X of the insertion cord 3 and are distributed in a circumferential direction thereof. FIG. 8 shows a device connecting the first, second and third steering wires 12*a*, 12*b*, 12*c* to the first and second control wheels 11*a*, 11*b*, which are selectively engageable to the control shaft 9 via the steering switch mechanism 13 according to FIGS. 1 to 6C. In FIG. 8, the first and second control wheels 11*a*, 11*b*, which are arranged coaxially with the control shaft 9, are shown next to each other for better illustration. The first control wheel 11*a* has a first wheel portion 27*a* connected to the first steering wire 12*a* and a second wheel portion 28*a* connected to one end of a connecting wire 29. The second control wheel 11*b* has a third wheel portion 27*b* connected to the second steering wire 12*b* and a fourth wheel portion 28*b* connected to another end of the connecting wire 29. The connecting wire 29 extends distally from the second wheel portion 28*a*, is guided around a passive wheel or drum serving as a redirecting member 30 and then extends proximally to the second control wheel 11*b*. The redirecting member 30 is connected to a proximal end portion of the third steering wire 12*b*.

By selectively rotating one among the first and second control wheels 11*a*, 11*b* while braking the other one among the first and second control wheels 11*a*, 11*b* via the steering switch mechanism 13, the bending section 5 is bent. Rotating directions R1, R2, R3 and R4 which correspond to four bending directions d1, d2, d3 and d4 shown in FIG. 7 are indicated by corresponding arrows in FIG. 8. When only the first control wheel 11*a* is rotated according to arrow R1 (or respectively R2), the first steering wire 12*a* is wound on (or respectively unwound from) the first wheel portion 27*a* and the connecting wire 29 is unwound from (or respectively wound on) the second wheel portion 28*a*, such that the bending section 5 is bent in the first (or respectively third) bending direction d1 (*d*3), i.e. in one of the bending planes. When only the second control wheel 11*b* is rotated according to arrow R2 (or respectively R4), the second steering wire 12*b* is wound on (or respectively unwound from) the second wheel portion 27*b* and the connecting wire 29 is unwound from (or respectively wound on) the fourth wheel portion 28*b*, such that the bending section 5 is bent in the second (or respectively fourth) bending direction d2 (d4), i.e. in the other one of the bending planes.

The following items are further variations and examples of the embodiments described above:

1. An endoscope (1) comprising: a proximal endoscope handle (2); an insertion cord (3) extending from the endoscope handle (2) and configured to be inserted into a patient's body cavity, the insertion cord (3) comprising an insertion tube (4), a bending section (5) and a distal tip unit (6); and a steering mechanism configured to swivel the distal tip unit (6) by bending the bending section (5) in a first bending plane and in a second bending plane, the steering mechanism comprising: a manually operable steering input element (7) being provided for receiving a rotational input by a user; and a steering switch mechanism (13) configured to switch a coupling state of the steering input element (7) between at least a first mode of operation, in which the steering mechanism is configured for bending the bending section (5) in the first bending plane via the steering input element (7), and a second mode of operation, in which the steering mechanism is configured for bending the bending section (5) in the second bending plane via the steering input element (7).

2. The endoscope (1) according to item 1, wherein the steering mechanism further comprises a first control wheel (11*a*) connected to a first steering wire (12*a*), which extends through the insertion cord (3) and is provided for controlling a bending movement of the bending section (5) in the first bending plane, and a second control wheel (11*b*) connected to a second steering wire (12*b*), which extends through the insertion cord (3) and is provided for controlling a bending movement of the bending section (5) in the second bending plane, and wherein the steering switch mechanism (13) comprises a first coupling portion (16*a*) formed between the steering input element (7) and the first control wheel (11*a*) and adapted for coupling the steering input element (7) to the first control wheel (11*a*), and a second coupling portion (16*b*) formed between the steering input element (7) and the second control wheel (11*b*) and adapted for coupling the steering input element (7) to the second control wheel (11*b*); and wherein the manually operable steering input element (7) is connected to a control shaft (9), which is rotatably supported at the endoscope handle (2).

3. The endoscope (1) according to item 2, wherein the steering switch mechanism (13) further has a first braking portion (20*a*) adapted to connect a housing of the endoscope handle (2) to the first control wheel (11*a*) for braking said first control wheel (11*a*) and a second braking portion (20*b*) adapted to connect the housing of the endoscope handle (2) to the second control wheel (11*b*) for braking said second control wheel (11*b*).

4. The endoscope (1) according to item 3, wherein the steering switch mechanism (13) further comprises a first biasing element (24*a*) biasing the first control wheel (11*a*) to the housing of the endoscope handle (2) such that at least the first braking portion (20*a*) is biased to be closed.

5. The endoscope (1) according item 3 or 4, wherein the steering switch mechanism (13) is further adapted to switch a coupling state of the steering input element (7) to a neutral state, in which the first braking portion (20*a*) and the second braking portion (20*b*) are closed to brake the first control wheel (11*a*) and the second control wheel (11*b*), and in which the first coupling portion (16*a*) and the second coupling portion (16*b*) are open and uncoupled from the steering input element (7).

6. The endoscope (1) according to item 5, wherein, when the steering switch mechanism (13) is in the neutral state, a side of the first control wheel (11*a*) and a side of the second control wheel (11*b*) are arranged essentially symmetrically with respect each other.

7. The endoscope (1) according to any one of the items 3 to 6, wherein the first control wheel (11*a*) forms a first wheel side braking surface (20*a*) adapted to connect to a first handle side braking surface (19*a*) as part of the first braking portion (20*a*), and a first wheel side coupling surface (17*a*) adapted to connect to a first shaft side coupling surface (18*a*) as part of the first coupling portion (16*a*), with the first wheel side braking surface (20*a*) and the first wheel side coupling surface (17*a*) being oriented in a first axial direction.

8. The endoscope (1) according to item 7, wherein a first distance between the first wheel side coupling surface (17*a*) and the first wheel side braking surface (20*a*) of the first control wheel (11*a*) is shorter than a second distance between the first shaft side coupling surface (18*a*) and the first handle side braking surface (19*a*) in the neutral state.

9. The endoscope (1) according to any one of the items 2 to 8, wherein the first control wheel (11*a*) and the second control wheel (11*b*) are axially translatable relative to the control shaft (9) and to the endoscope handle (2).

10. The endoscope (1) according to any one of the items 2 to 9, wherein the steering switch mechanism (13) comprises a manually operable switch input device (8) being provided for receiving an input by a user, and a shifting element (14) being shiftably supported at the endoscope handle (2) to be axially shiftable relative to the control shaft (9) between a first position, in which the first coupling portion (16*a*) is closed and couples the steering input element (7) to the first control wheel (11*a*), and a second position, in which the second coupling portion (16*b*) is closed and couples the steering input element (7) to the second control wheel (11*b*).

11. The endoscope (1) according to item 10, wherein the shifting element (14) is a cage or casing accommodating the first control wheel (11*a*) and the second control wheel (11*b*).

12. The endoscope (1) according to item 10 or 11, wherein the steering switch mechanism (13) is actuated via a lever rotatably supported at the endoscope handle (2), particularly coaxially to the steering input element (7), and being connected to the shifting element (14) via a transmission structure, preferably including a ramp surface, to transform a rotational input by the user into an axial shifting of the shifting element (14).

13. The endoscope (1) according to item 10 or 11, wherein the steering switch mechanism (13) is actuated via a slider which is slidably supported in the endoscope handle (2) and has two opposing ends which extend from the endoscope handle (2) for receiving the input by the user, with the slider being connected to the shifting element (14), preferably via transmission rods (23), for transforming a sliding movement of the slider into a shifting movement of the shifting element (14).

14. The endoscope (1) according to item 10 or 11, wherein the steering switch mechanism (13) is actuated via the steering input element (7), with the steering input element (7) being supported to be axially translatable relative to the endoscope handle (2) and being integrally formed with or connected to the shifting element (14) in order to transform a translational movement of the steering input element (7) into a shifting movement of the shifting element (14).

15. A system comprising an endoscope (1) according to any one of the items 1 to 14 and a monitor (M) connectable to the endoscope (1).

LIST OF REFERENCE NUMBERS

1 Endoscope
2 Endoscope handle
3 Insertion cord
4 Insertion tube
5 Bending section
6 Distal tip unit
7 Steering input element/hand wheel
8 Switch input element/lever
9 Control shaft
10 Supporting flange
11*a*, 11*b* First and second control wheels
12*a*, 12*b*, 12*c* First, second and third steering wires
13 Steering switch mechanism
14 Shifting element/cage/casing
15 Transmission structure/ramp surface
16*a*, 16*b* First and second coupling portions

17*a*, 17*b* First and second friction fit arrangements (stacks of friction discs)
18*a*, 18*b* First and second shaft side coupling surfaces
19*a*, 19*b* First and second wheel side coupling surfaces
20*a*, 20*b* First and second braking portions
21*a*, 21*b* Third and fourth friction fit arrangements (stacks of friction discs)
22*a*, 22*b* First and second handle side braking surfaces
23*a*, 23*b* First and second wheel side braking surfaces
24*a*, 24*b* First and second biasing elements/first and second springs
25 Transmission rods
26 Chain
27*a* First wheel portion
27*b* Third wheel portion
28*a* Second wheel portion
28*b* Fourth wheel portion
29 Connecting wire
30 Redirecting member
M Monitor
Fb Braking force flow
Fo Operating force flow
d1-d4 First to fourth bending directions
R1-R4 Rotating directions

I claim:

1. An endoscope comprising:
an endoscope handle;
an insertion cord extending from the endoscope handle and including an insertion tube, a bending section and a distal tip; and
a steering mechanism comprising a steering wheel and a steering switch mechanism, the steering mechanism having a first mode of operation, in which rotation of the steering wheel causes bending of the bending section in a first bending plane, and a second mode of operation, in which rotation of the steering wheel causes bending of the bending section in a second bending plane,
the steering wheel being rotatably supported by the endoscope handle and manually operable by a user; and
the steering switch mechanism being configured to switch the steering mechanism between the first mode of operation and the second mode of operation.

2. The endoscope of claim 1, further comprising a control shaft and a switch input device, the control shaft connected to the steering wheel and rotatably supported at the endoscope handle, and the switch input device being manually operable to receive a switching input by the user, the switch input device switching the steering mechanism between the first mode of operation and the second mode of operation, based on the switching input.

3. The endoscope of claim 2, wherein the switch input device comprises a lever rotatably supported at the endoscope handle coaxially to the steering wheel.

4. The endoscope of claim 1, further comprising a control shaft connected to the steering wheel and rotatably supported at the endoscope handle,
wherein the steering mechanism further comprises:
a first control wheel connected to a first steering wire, which extends through the insertion cord and is configured to bend the bending section in the first bending plane, and
a second control wheel connected to a second steering wire, which extends through the insertion cord and is configured to bend the bending section in the second bending plane,
wherein the steering switch mechanism comprises:
a first coupling portion formed between the steering wheel and the first control wheel and configured to couple the steering wheel to the first control wheel, and
a second coupling portion formed between the steering wheel and the second control wheel and configured to couple the steering wheel to the second control wheel.

5. The endoscope of claim 4, wherein the first control wheel and the second control wheel are axially translatable relative to the control shaft and to the endoscope handle.

6. The endoscope of claim 4, wherein the steering switch mechanism further has a first braking portion adapted to connect a housing of the endoscope handle to the first control wheel for braking said first control wheel and a second braking portion adapted to connect the housing of the endoscope handle to the second control wheel for braking said second control wheel.

7. The endoscope of claim 6, wherein the steering switch mechanism further comprises a first biasing element biasing the first control wheel to the housing of the endoscope handle such that at least the first braking portion is biased to be closed.

8. The endoscope of claim 6, wherein the steering wheel has a first coupling state, a second coupling state, and a neutral state, wherein in the first coupling state the steering mechanism is in the first mode of operation, wherein in the second coupling state the steering mechanism is in the second mode of operation, and wherein the steering switch mechanism is further adapted to switch the steering wheel to the neutral state, in which the first braking portion and the second braking portion are closed to brake the first control wheel and the second control wheel, and in which the first coupling portion and the second coupling portion are open and uncoupled from the steering wheel.

9. The endoscope of claim 8, wherein, when the steering wheel is in the neutral state, a side of the first control wheel and a side of the second control wheel are arranged symmetrically with respect each other.

10. The endoscope of claim 6, wherein the first control wheel forms a first wheel side braking surface adapted to connect to a first handle side braking surface as part of the first braking portion, and a first wheel side coupling surface adapted to connect to a first shaft side coupling surface as part of the first coupling portion, with the first wheel side braking surface and the first wheel side coupling surface being oriented in a first axial direction.

11. The endoscope of claim 10, wherein a first distance between the first wheel side coupling surface and the first wheel side braking surface of the first control wheel is shorter than a second distance between the first shaft side coupling surface and the first handle side braking surface in a neutral state of the steering wheel.

12. The endoscope of claim 4, wherein the steering switch mechanism further comprises:
a switch input device manually operable to receive a switching input by the user, and
a shifting element being shiftably supported at the endoscope handle to be axially shiftable relative to the control shaft between a first position, in which the first coupling portion is closed and couples the steering wheel to the first control wheel, and a second position, in which the second coupling portion is closed and couples the steering wheel to the second control wheel.

13. The endoscope of claim 12, wherein the shifting element is a cage or casing accommodating the first control wheel and the second control wheel.

14. The endoscope of claim 12, wherein the switch input device comprises a lever rotatably supported at the endoscope handle and being connected to the shifting element via a transmission structure to transform a rotational input by the user into an axial shifting of the shifting element.

15. The endoscope of claim 14, wherein the lever is supported coaxially to the steering wheel.

16. The endoscope of claim 14, wherein the transmission structure includes a ramp surface to transform the rotational input into the axial shifting of the shifting element.

17. The endoscope of claim 12, wherein the switch input device comprises a slider which is slidably supported in the endoscope handle and has two opposing ends which extend from the endoscope handle for receiving the switching input by the user, with the slider being connected to the shifting element for transforming a sliding movement of the slider into a shifting movement of the shifting element.

18. The endoscope of claim 17, further comprising transmission rods coupling the slider to the shifting element.

19. The endoscope of claim 12, wherein the steering switch mechanism is actuated via the steering wheel, with the steering wheel being supported to be axially translatable relative to the endoscope handle and being integrally formed with or connected to the shifting element to transform a translational movement of the steering wheel into a shifting movement of the shifting element.

20. An endoscope system comprising:

a monitor; and an endoscope according to claim 1, the endoscope further comprising a camera located at a distal end of the endoscope, wherein the endoscope is connectable to the monitor, and wherein the monitor is configured for displaying an image captured by the camera.

* * * * *